United States Patent
Bardy et al.

(10) Patent No.: US 6,856,835 B2
(45) Date of Patent: Feb. 15, 2005

(54) BIPHASIC WAVEFORM FOR ANTI-TACHYCARDIA PACING FOR A SUBCUTANEOUS IMPLANTABLE CARDIOVERTER-DEFIBRILLATOR

(75) Inventors: Gust H. Bardy, Seattle, WA (US); Riccardo Cappato, Ferrara (IT); William J. Rissmann, Coto de Caza, CA (US)

(73) Assignee: Cameron Health, Inc., San Clemente, CA (US)

( * ) Notice: Subject to any disclaimer, the term of this patent is extended or adjusted under 35 U.S.C. 154(b) by 223 days.

(21) Appl. No.: 09/940,266

(22) Filed: Aug. 27, 2001

(65) Prior Publication Data

US 2002/0035376 A1 Mar. 21, 2002

Related U.S. Application Data

(63) Continuation-in-part of application No. 09/663,607, filed on Sep. 18, 2000, and a continuation-in-part of application No. 09/663,606, filed on Sep. 18, 2000, now Pat. No. 6,647,292.

(51) Int. Cl.$^7$ .............................................. A61N 1/368
(52) U.S. Cl. .............................................. 607/14; 607/9
(58) Field of Search ........................... 607/4, 9, 11, 14, 607/29

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,157,720 A | 6/1979 | Greatbatch |
| 4,191,942 A | 3/1980 | Long |
| 4,223,678 A | 9/1980 | Langer et al. |
| 4,248,237 A | 2/1981 | Kenny |
| 4,291,707 A | 9/1981 | Heilman et al. |

(List continued on next page.)

FOREIGN PATENT DOCUMENTS

| | | |
|---|---|---|
| DE | 298 01 807 U1 | 7/1998 |
| EP | 0 095 727 A1 | 12/1983 |

(List continued on next page.)

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361–362.

(List continued on next page.)

*Primary Examiner*—Kennedy Schaetzle
*Assistant Examiner*—Kristen Mullen
(74) *Attorney, Agent, or Firm*—Crompton, Seager & Tufte, LLC

(57) ABSTRACT

A power supply for an implantable cardioverter-defibrillator for subcutaneous positioning between the third rib and the twelfth rib and using a lead system that does not directly contact a patient's heart or reside in the intrathorasic blood vessels and for providing anti-tachycardia pacing energy to the heart, comprising a capacitor subsystem for storing the anti-tachycardia pacing energy for delivery to the patient's heart; and a battery subsystem electrically coupled to the capacitor subsystem for providing the anti-tachycardia pacing energy to the capacitor subsystem.

15 Claims, 9 Drawing Sheets

U.S. PATENT DOCUMENTS

| | | | |
|---|---|---|---|
| 4,314,095 A | | 2/1982 | Moore et al. |
| 4,402,322 A | | 9/1983 | Duggan |
| 4,406,286 A | * | 9/1983 | Stein .......................... 607/13 |
| 4,407,288 A | | 10/1983 | Langer et al. |
| 4,412,541 A | * | 11/1983 | Schaldach et al. ............. 607/9 |
| 4,424,818 A | | 1/1984 | Doring et al. |
| 4,543,956 A | * | 10/1985 | Herscovici .................. 607/13 |
| 4,602,637 A | | 7/1986 | Elmqvist et al. |
| 4,765,341 A | | 8/1988 | Mower et al. |
| 4,800,883 A | | 1/1989 | Winstrom |
| 4,830,005 A | | 5/1989 | Woskow |
| 5,109,842 A | | 5/1992 | Adinolfi |
| 5,129,392 A | | 7/1992 | Bardy et al. |
| 5,133,353 A | | 7/1992 | Hauser |
| 5,144,946 A | | 9/1992 | Weinberg et al. |
| 5,184,616 A | | 2/1993 | Weiss |
| 5,191,901 A | | 3/1993 | Dahl et al. |
| 5,203,348 A | | 4/1993 | Dahl et al. |
| 5,230,337 A | | 7/1993 | Dahl et al. |
| 5,255,692 A | | 10/1993 | Neubauer et al. |
| 5,261,400 A | | 11/1993 | Bardy |
| 5,261,401 A | * | 11/1993 | Baker et al. .................... 607/9 |
| 5,300,106 A | | 4/1994 | Dahl et al. |
| 5,318,591 A | * | 6/1994 | Causey et al. ................. 607/5 |
| 5,331,966 A | | 7/1994 | Bennett et al. |
| 5,342,407 A | | 8/1994 | Dahl et al. |
| 5,366,496 A | | 11/1994 | Dahl et al. |
| 5,376,103 A | | 12/1994 | Anderson et al. |
| 5,376,104 A | | 12/1994 | Sakai et al. |
| 5,385,574 A | | 1/1995 | Hauser et al. |
| 5,391,200 A | | 2/1995 | KenKnight et al. |
| 5,411,539 A | | 5/1995 | Neisz |
| 5,411,547 A | | 5/1995 | Causey, III |
| 5,413,591 A | | 5/1995 | Knoll |
| 5,447,519 A | * | 9/1995 | Peterson ....................... 607/5 |
| 5,509,923 A | | 4/1996 | Middleman et al. |
| 5,509,928 A | | 4/1996 | Acken |
| 5,531,765 A | | 7/1996 | Pless |
| 5,531,766 A | | 7/1996 | Kroll et al. |
| 5,534,019 A | | 7/1996 | Paspa |
| 5,601,607 A | | 2/1997 | Adams |
| 5,603,732 A | | 2/1997 | Dahl et al. |
| 5,618,287 A | | 4/1997 | Fogarty et al. |
| 5,620,477 A | | 4/1997 | Pless et al. |
| 5,643,328 A | | 7/1997 | Cooke et al. |
| 5,645,586 A | | 7/1997 | Meltzer |
| 5,658,317 A | | 8/1997 | Haefner et al. |
| 5,674,260 A | | 10/1997 | Weinberg |
| 5,690,648 A | | 11/1997 | Fogarty et al. |
| 5,690,683 A | | 11/1997 | Haefner et al. |
| 5,697,953 A | | 12/1997 | Kroll et al. |
| 5,713,926 A | | 2/1998 | Hauser et al. |
| 5,766,226 A | | 6/1998 | Pedersen |
| 5,776,169 A | | 7/1998 | Schroeppel |
| 5,814,090 A | | 9/1998 | Latterell et al. |
| 5,836,976 A | | 11/1998 | Min et al. |
| 5,895,414 A | | 4/1999 | Sanchez-Zambrano |
| 5,919,211 A | | 7/1999 | Adams |
| 5,919,222 A | | 7/1999 | Hjelle et al. |
| 5,925,069 A | | 7/1999 | Graves et al. |
| 5,935,154 A | | 8/1999 | Westlund |
| 5,941,904 A | | 8/1999 | Johnston et al. |
| 5,964,787 A | * | 10/1999 | Kerver et al. .................. 607/9 |
| 6,014,586 A | | 1/2000 | Weinberg et al. |
| 6,026,325 A | | 2/2000 | Weinberg et al. |
| 6,058,328 A | | 5/2000 | Levine et al. |
| 6,093,173 A | | 7/2000 | Balceta et al. |
| 6,095,987 A | | 8/2000 | Shmulewitz et al. |
| H1905 H | | 10/2000 | Hill |
| 6,128,531 A | | 10/2000 | Campbell-Smith |
| 6,144,866 A | | 11/2000 | Miesel et al. |
| 6,148,230 A | * | 11/2000 | KenKnight .................. 600/516 |
| 6,185,450 B1 | | 2/2001 | Seguine et al. |
| 6,411,844 B1 | | 6/2002 | Kroll et al. |
| 6,519,493 B1 | * | 2/2003 | Florio et al. ................... 607/9 |
| 2001/0027330 A1 | | 10/2001 | Sullivan et al. |

FOREIGN PATENT DOCUMENTS

| | | |
|---|---|---|
| EP | 0 316 616 A2 A3 | 5/1989 |
| EP | 0 347 353 A1 | 12/1989 |
| EP | 0 517 494 B1 | 12/1992 |
| EP | 0 517 494 A3 | 12/1992 |
| EP | 0 518 599 B1 | 12/1992 |
| EP | 0 518 599 A2 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A3 | 3/1995 |
| EP | 0 641 573 A2 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A3 | 3/2002 |
| WO | WO 02/22208 A2 | 3/2002 |
| WO | WO 02/24275 A3 | 3/2002 |
| WO | WO 02/24275 A2 | 3/2002 |
| WO | WO 02/068046 A1 | 9/2002 |
| WO | WO 03/018121 A2 | 3/2003 |

OTHER PUBLICATIONS

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356–360.

Mirowski, M. et al., "Automatic Detection and Defibrillation of Lethal Arrhythmias—A New Concept," *JAMA*, vol. 213, No. 4, Jul. 27, 1970, pp. 615–616.

Olson, Walter H. et al., "Onset and Stability for Ventricular Tachyarrhythmia Detection in an Implanatable Pacer–Cardioverter–Defribrillator," *IEEE*, (1987) pp. 167–170.

Schuder, John C., "Completely Implanted Defibrillator," *JAMA*, vol. 214, No. 6, Nov. 9, 1970, p. 1123 (single sheet).

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95–124.

Schuder, John C. et al., "Experimental Ventricular Defibrillation with an Automatic and Completely Implanted System," *Trans. Amer. Soc. Artif. Int, Organs*, vol. XVI (1970) pp. 207–212.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio–Medical Engineering*, vol. BME–18, No. 6, Nov. 1971, pp . 410–415.

Tietze U. et al., "Halbleiter–Schaltungstechnik," © Springer–Verlag (Berlin, Germany), (1991), pp. 784–786.

Walters, R.A. et al., "Analog to Digital Conversion Techniques in Implantable Devices," *Annual International Conference of the IEEE Engineering in Medicine and Biology Society*, vol. 13 No. 4 (1991) Pg. 1674–1676.

* cited by examiner

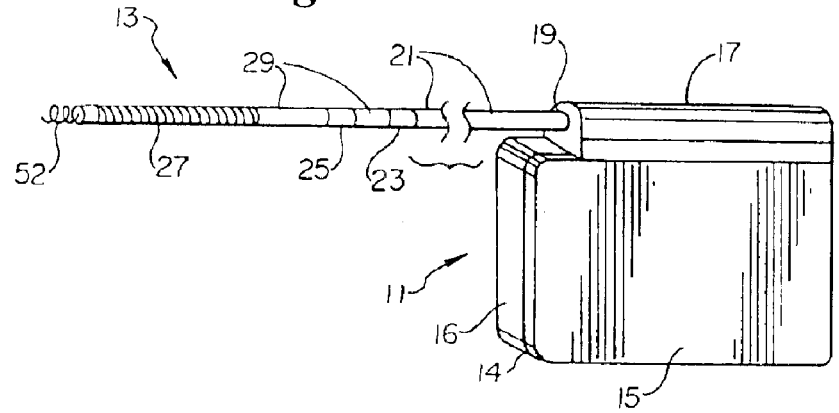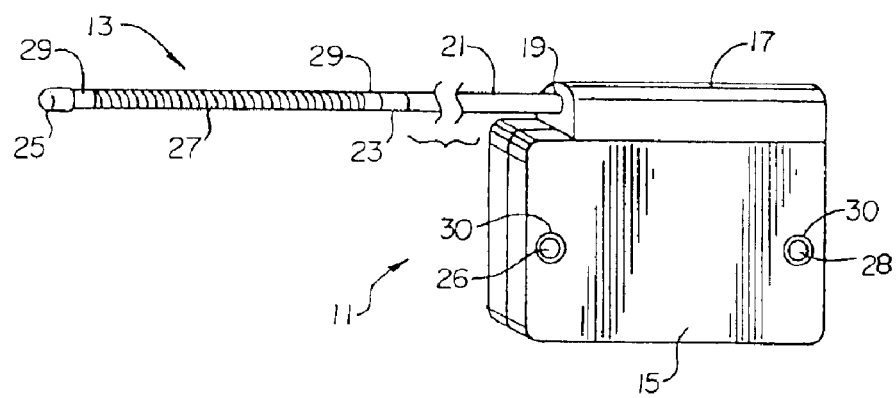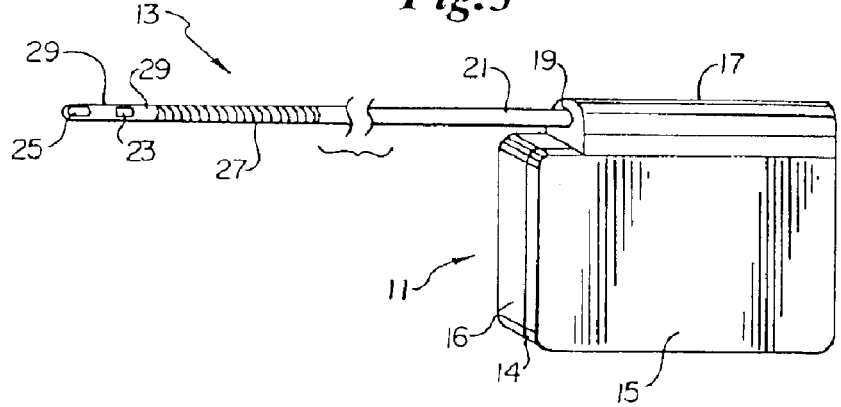

BIPHASIC WAVEFORM FOR ANTI-TACHYCARDIA PACING FOR A SUBCUTANEOUS IMPLANTABLE CARDIOVERTER-DEFIBRILLATOR

CROSS-REFERENCE TO RELATED APPLICATIONS

The present application is a continuation-in-part of U.S. patent application entitled "SUBCUTANEOUS ONLY IMPLANTABLE CARDIOVERTER-DEFIBRILLATOR AND OPTIONAL PACER," having Ser. No. 09/663,606, filed Sep. 18, 2000, now U.S. Pat. No. 6,647,292, and U.S. patent application entitled "UNITARY SUBCUTANEOUS ONLY IMPLANTABLE CARDIOVERTER-DEFIBRILLATOR AND OPTIONAL PACER," having Ser. No. 09/663,607, filed Sep. 18, 2000, pending, of which both applications are assigned to the assignee of the present application, and the disclosures of both applications are hereby incorporated by reference.

In addition, the present application is filed concurrently herewith U.S. patent application entitled "DUCKBILL-SHAPED IMPLANTABLE CARDIOVERTER-DEFIBRILLATOR AND METHOD OF USE," U.S. patent application entitled "CERAMICS AND/OR OTHER MATERIAL INSULATED SHELL FOR ACTIVE AND NON-ACTIVE S-ICD CAN," U.S. patent application entitled "SUBCUTANEOUS ELECTRODE FOR TRANSTHORACIC CONDUCTION WITH IMPROVED INSTALLATION CHARACTERISTICS," U.S. patent application entitled "SUBCUTANEOUS ELECTRODE WITH IMPROVED CONTACT SHAPE FOR TRANSTHORACIC CONDUCTION," U.S. patent application entitled "SUBCUTANEOUS ELECTRODE FOR TRANSTHORACIC CONDUCTION WITH HIGHLY MANEUVERABLE INSERTION TOOL," U.S. patent application entitled "SUBCUTANEOUS ELECTRODE FOR TRANSTHORACIC CONDUCTION WITH LOW-PROFILE INSTALLATION APPENDAGE AND METHOD OF DOING SAME," U.S. patent application entitled "SUBCUTANEOUS ELECTRODE FOR TRANSTHORACIC CONDUCTION WITH INSERTION TOOL," U.S. patent application entitled "METHOD OF INSERTION AND IMPLANTATION FOR IMPLANTABLE CARDIOVERTER-DEFIBRILLATOR CANISTERS," U.S. patent application entitled "CANISTER DESIGNS FOR IMPLANTABLE CARDIOVERTER-DEFIBRILLATORS," U.S. patent application entitled "RADIAN CURVED IMPLANTABLE CARDIOVERTER-DEFIBRILLATOR CANISTER," U.S. patent application entitled "CARDIOVERTER-DEFIBRILLATOR HAVING A FOCUSED SHOCKING AREA AND ORIENTATION THEREOF," U.S. patent application entitled "BIPHASIC WAVEFORM FOR ANTI-BRADYCARDIA PACING FOR A SUBCUTANEOUS IMPLANTABLE CARDIOVERTER-DEFIBRILLATOR," and U.S. patent application "POWER SUPPLY FOR A SUBCUTANEOUS IMPLANTABLE CARDIOVERTER-DEFIBRILLATOR," the disclosures of which applications are hereby incorporated by reference.

FIELD OF THE INVENTION

The present invention relates to an apparatus and method for performing electrical cardioversion/defibrillation and optional anti-tachycardia pacing of the heart via a totally subcutaneous non-transvenous system.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes and are referred to as implantable cardioverter/defibrillators (ICDs). Such electrodes can be in the form of patches applied directly to epicardial tissue, or at the distal end regions of intravascular catheters, inserted into a selected cardiac chamber. U.S. Pat. Nos. 4,603,705, 4,693,253, 4,944,300, 5,105,810, the disclosures of which are all incorporated herein by reference, disclose intravascular or transvenous electrodes, employed either alone or in combination with an epicardial patch electrode. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has o practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261, 400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of automatic external defibrillator (AED) therapy. AEDs employ the use of cutaneous patch electrodes to effect defibrillation under the direction of a bystander user who treats the patient suffering from V-Fib. AEDs can be as effective as an ICD if applied to the victim promptly within 2 to 3 minutes.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

Ventricular tachycardia ("VT") is a relatively common and serious cardiac rhythm disorder in patients with serious heart disease. VT may lead to symptoms of shortness of breath, chest pain, loss of consciousness and even death. VT, like ventricular fibrillation, can usually be terminated with a high-energy electrical shock. Unlike ventricular fibrillation, however, VT, especially VT with a regular rate and ECG pattern, can, on some occasions, be terminated with a type of pacing called anti-tachycardia pacing ("ATP"). Cardioversion/defibrillation of VT is done with high-energy shocks, which usually is very uncomfortable, albeit potentially life-saving. ATP, on the other hand can stop VT painlessly with relatively low energy electrical stimuli, similar to standard pacing pulses as used in standard pacemakers. Conventional ICDs often use ATP to avoid the need to shock-terminate VT, in some cases of VT. ATP can be of several types, all of which use electrical stimuli delivered at rates faster than the intrinsic or native VT rate in order to "over-drive" the VT and take control of the electrical mechanism of the heart causing the VT. ATP is possible because VT is similar in nature to ATP, except one is intrinsic to the heart and one is artificially generated with a pacemaker. ATP merely over-drives the patient's rapid pacemaker (i.e., VT), usurps control of the heart rhythm, then abruptly ceases to control the heart rhythm. This process can all be directed by the physician who programs the ATP modes in the implantable device. Once ATP usurps control of the heart rhythm from the patient's VT mechanism, and once ATP stops, the patient's rhythm can then return to normal.

ATP will work in about 75% of the cases with monomorphic VT (i.e., VT having a regular rate and ECG pattern) and being at rates typically under 250 beats per minute. There are several types of methods for overdriving the patient's VT. Most derive from two general forms. One is called "burst" ATP. The other is termed "ramp" ATP.

In burst ATP, the device is asked to deliver pacing stimuli of a certain number, typically around 5–15, at a rate that is modestly to moderately faster than the rate of the patient's VT. This rate is fixed for any attempt and the interval between pacing stimuli is constant. In some forms of burst pacing, if the first attempt fails to terminate VT, the next attempt may be slightly faster, according to pre-selected parameters as dictated by the software of the device or by the physician. The physician may program a maximum rate that could be allowed with ATP.

In ramp ATP, the device is asked to deliver pacing stimuli of a certain number, again typically around 5–15, also starting at a rate that is modestly to moderately faster than the rate of the patient's VT. Unlike burst ATP, however, ramp ATP does not use a fixed rate for each attempt. In ramp ATP, for any given attempt, the interval between pacing stimuli gets progressively shorter, i.e., the pacing rate gets progressively faster. As in some forms of burst ATP, if the first attempt of ramp ATP fails to terminate VT, the next attempt may be slightly faster, add more pacing stimuli, change the coupling intervals between pacing stimuli and/or add more attempts as guided by pre-selected parameters as dictated by the software of the device or by the physician.

Conventional ICDs can also use a variety of combinations of these two basic forms of ATP, but the principle remains the same. Stimulate the heart with a low-energy pacing pulse that can over-drive the patient's VT which can, thereafter stop according to device and physician directions to leave the heart with its normal rhythm that existed before the onset of the VT episode.

SUMMARY OF THE INVENTION

A power supply for an implantable cardioverter-defibrillator for subcutaneous positioning between the third rib and the twelfth rib and using a lead system that does not directly contact a patient's heart or reside in the intrathoracic blood vessels and for providing anti-tachycardia pacing energy to the heart, comprising a capacitor subsystem for storing the anti-tachycardia pacing energy for delivery to the patient's heart; and a battery subsystem electrically coupled to the capacitor subsystem for providing the anti-tachycardia pacing energy to the capacitor subsystem.

BRIEF DESCRIPTION OF THE DRAWINGS

For a better understanding of the invention, reference is now made to the drawings where like numerals represent similar objects throughout the figures where:

FIG. 1 is a schematic view of a Subcutaneous ICD (S-ICD) of the present invention;

FIG. 2 is a schematic view of an alternate embodiment of a subcutaneous electrode of the present invention;

FIG. 3 is a schematic view of an alternate embodiment of a subcutaneous electrode of the present invention;

DETAILED DESCRIPTION

Figure 4:
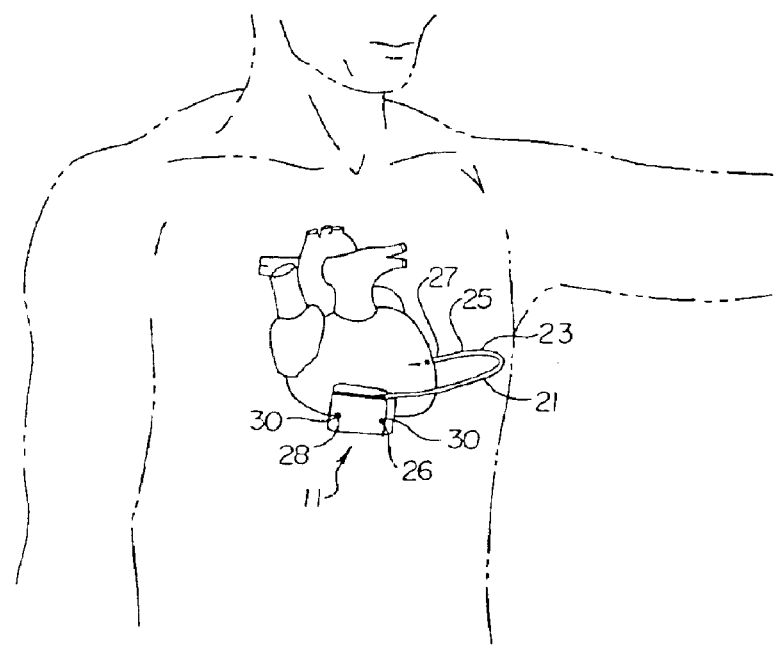
FIG. 4 is a schematic view of the S-ICD and lead of FIG. 1 subcutaneously implanted in the thorax of a patient.

Turning now to FIG. 1, the S-ICD of the present invention is illustrated. The S-ICD consists of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that the canister will contain a battery supply, capacitor and operational circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In the preferred embodiment, a 100 uF biphasic waveform is used of approximately 10–20 ms total duration and with the initial phase containing approximately ⅔ of the energy, however, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli will be biphasic in the preferred embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of a trial fibrillation as described in Olson, W. et al. "Onset And Stability For Ventricular Tachyarrhythmia Detection in an Implantable Cardioverter and Defibrillator," Computers in Cardiology (1986) pp. 167–170. Detection can be provided via R-R Cycle length instability detection algorithms. Once a trial fibrillation has been detected, the operational circuitry will then provide QRS synchronized a trial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R-R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patent is not respiring and this lack of respiration can be used to confirm the QRS findings of cardiac arrest. The same technique can be used to provide information about the respiratory rate or estimate cardiac output as described in U.S. Pat. Nos. 6,095,987, 5,423,326, 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long term wearability, especially in children. The canister and the lead of the S-ICD can also use fractal or wrinkled surfaces to increase surface area to improve defibrillation capability. Because of the primary prevention role of the therapy and the likely need to reach energies over 40 Joules, a feature of the preferred embodiment is that the charge time for the therapy, intentionally e relatively long to allow capacitor charging within the limitations of device size. Examples of small ICD housings are disclosed in U.S. Pat. Nos. 5,597,956 and 5,405,363, the entire disclosures of which are herein incorporated by reference.

Different subcutaneous electrodes 13 of the present invention are illustrated in FIGS. 1–3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5–10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 14 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein Incorporated by reference, disclosures a composite electrode with a coil cardioversion/defibrillation electrode and sense electrodes. Modifications to this arrangement are contemplated within the scope of the invention. One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist arid are contemplated within the present invention. For example, having only one sensing electrode, either proximal or distal to the coil cardioversion/defibrillation electrode with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000–5000 Volts with an associated maximum energy of approximately 200–360 Joules depending upon the model and waveform used. The S-ICD of the present invention uses maximum voltages in the range of about 700 to about 3150 Volts and is associated with energies of about 40 to about 210 Joules. The capacitance of the S-ICD could range from about 50 to about 200 micro farads.

The sense circuitry contained within the canister is highly sensitive and specific for the presence or absence of life threatening ventricular arrhythmias. Features of the detection algorithm are programmable and the algorithm is focused on the detection of V-FIB and high rate V-TACH (>240 bpm). Although the S-ICD of the present invention may rarely be used for an actual life threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Turning now to FIG. 4, the optimal subcutaneous placement of the S-ICD of the present invention is illustrated. As would be evidence to a person skilled in the art, the actual location of the S-ICD is in a subcutaneous space that is developed during the implantation process. The heart is not exposed during this process and the heart is schematically illustrated in the figures only for help in understanding where the canister and coil electrode are three dimensionally located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line ideally just lateral to the left scapula. This way the canister and subcutaneous cardioversion/defibrillation electrode provide a reasonably good pathway for current delivery to the majority of the ventricular myocardium.

Figure 5:
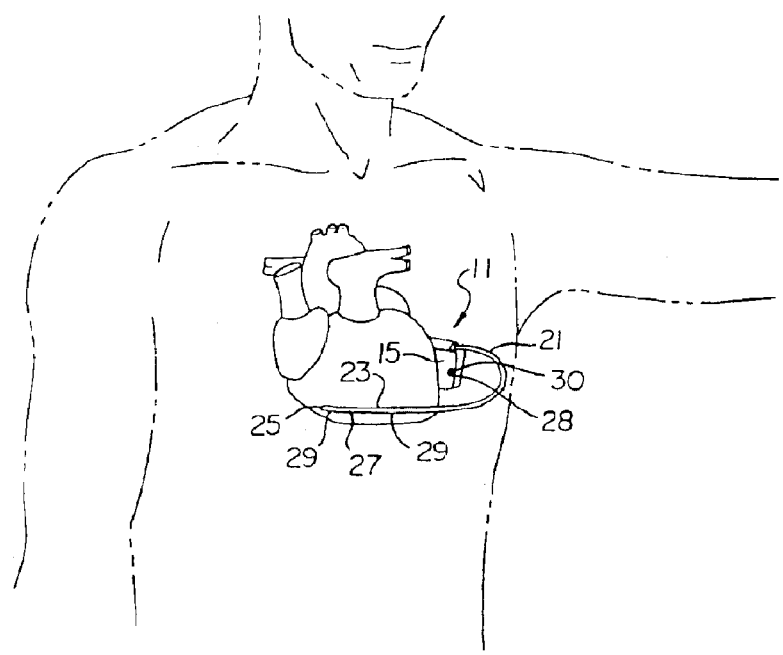
FIG. 5 is a schematic view of the S-ICD and lead of FIG. 2 subcutaneously implanted in an alternate location within the thorax of a patient.
Figure 6:
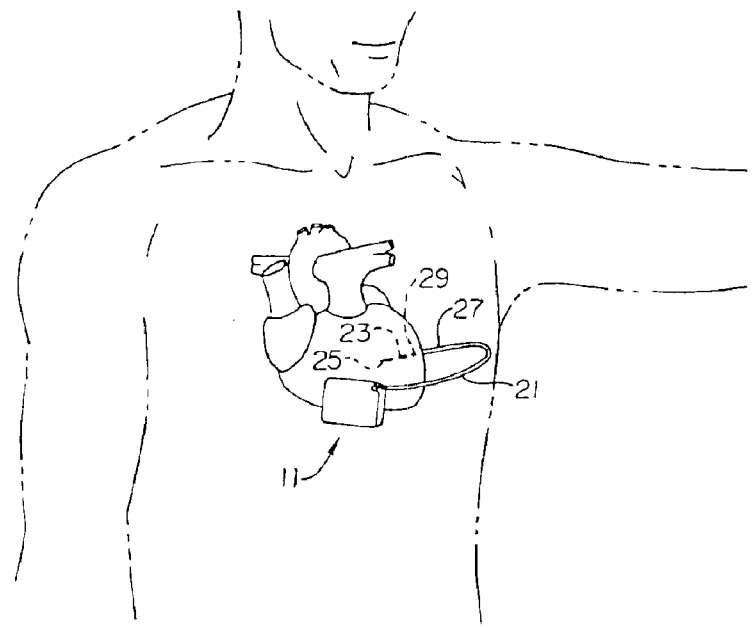
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
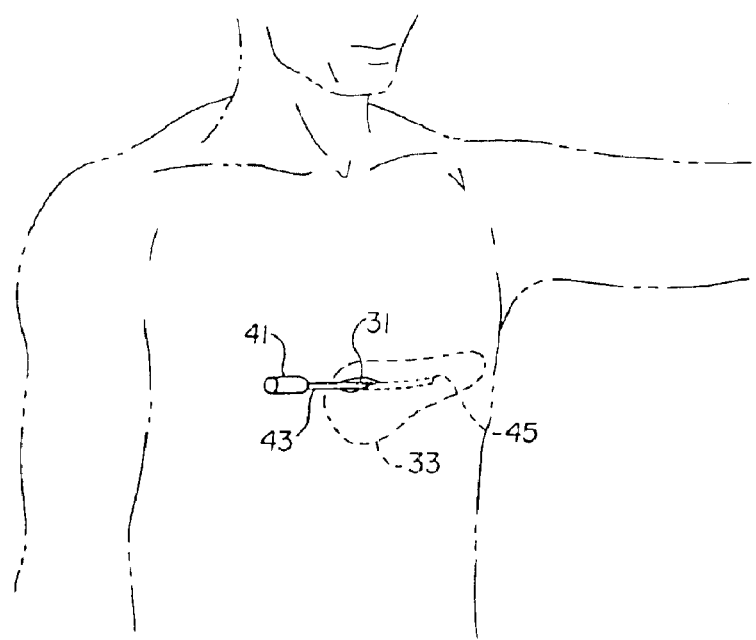
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision can be anywhere on the thorax deemed reasonably by the implanting physician although in the preferred embodiment the S-ICD of the present invention will be applied in this region. A subcutaneous pathway 33 is then created medially to the inframammary crease for the canister and posteriorly to the left posterior axillary line lateral to the left scapula for the lead.

Figure 8:
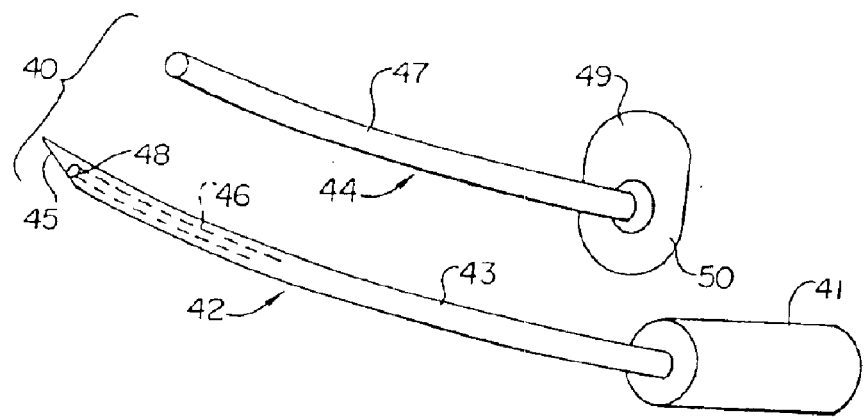
FIG. 8 is a schematic view of an introducer set for performing the method of lead insertion of any of the described embodiments.

The S-ICD canister 11 is then placed subcutaneously at the location of the incision or medially at the subcutaneous region at the left inframammary crease. The subcutaneous electrode 13 is placed with a specially designed curved introducer set 40 (sec FIG. 8). The introducer set comprises a curved trocar 42 and a stiff curved peel away sheath 44. The peel away sheath is curved to allow for placement around the rib cage of the patient in the subcutaneous apace created by the trocar. The sheath has to be stiff enough to allow for the placement of the electrodes without the sheath collapsing or bending. Preferably the sheath is made out of a biocompatible plastic material and is perforated along its axial length to allow for it to split apart into two sections. The trocar has a proximal handle 41 and a curved shaft 43. The distal end 45 of the trocar is tapered to allow for dissection of a subcutaneous path 33 in the patient. Preferably, the trocar is cannulated having a central Lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shaft 47. The sheath is placed over a guidewire inserted through the trocar after the subcutaneous path has been created. The subcutaneous pathway is then developed until it terminates subcutaneously at a location that, if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
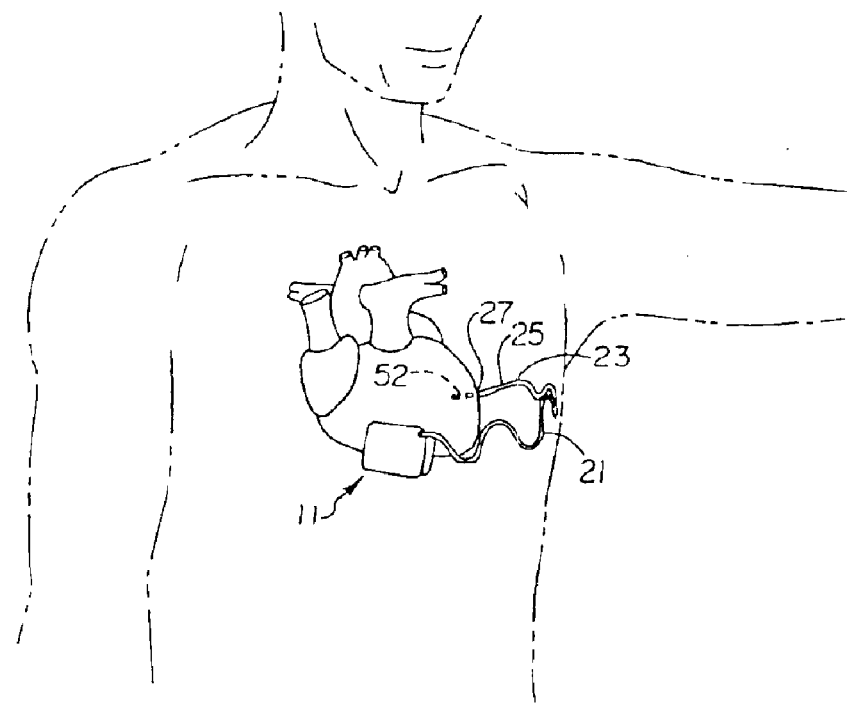
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial ICD lead systems pose excessive risk or have already resulted in difficulty, such as sepsis or lead fractures. It is also contemplated that a major use or the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that he problem that growth presents to the lead system is overcome. The distal end of the subcutaneous electrode is placed in the same location as described above providing a good location for the coil cardioversion/defibrillation electrode 27 and the sensing electrodes 23 and 25. The insulated lead 21, however, is no longer placed in a taut configuration. Instead, the lead is serpiginously placed with a specially designed introducer trocar and sheath such that it has numerous waves or bends. As the child grows, the waves or bends will straighten out lengthening the lead system while maintaining proper electrode placement. Although it is expected that fibrous scarring especially around the defibrillation coil will help anchor It into position to maintain its posterior position during growth, a lead system with a distal tine or screw electrode anchoring system 52 can also be Incorporated into the distal tip of the lead to facilitate lead stability (see FIG. 1). Other anchoring systems can also be used such as hooks sutures, or the like.

Figure 10:
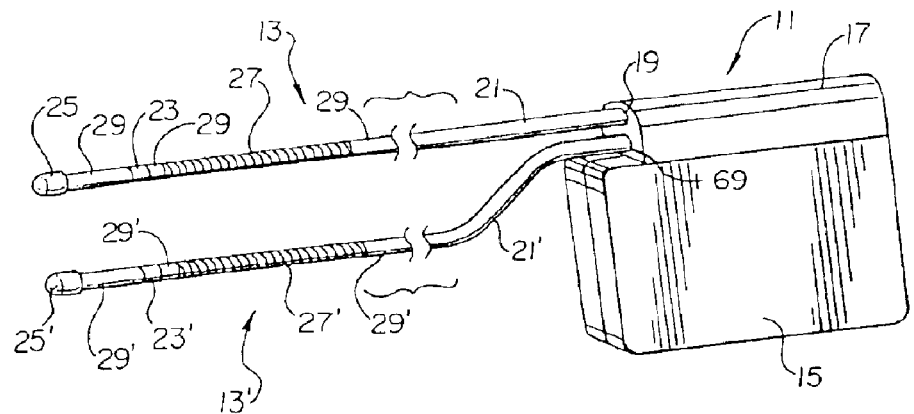
FIG. 10 is a schematic view of an alternate embodiment of an S-ICD of the present invention.
Figure 11:
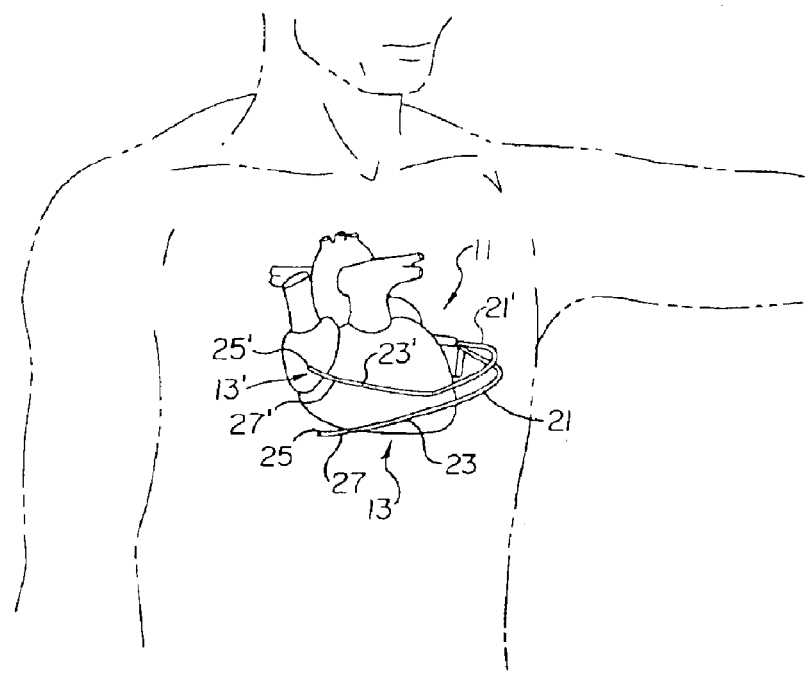
FIG. 11 is a schematic view of the S-ICD of FIG. 10 subcutaneously implanted in the thorax of a patient.

FIGS. 10 and 11 illustrate another embodiment of the present S-ICD invention. In this embodiment there are two subcutaneous electrodes 13 and 13' of opposite polarity to the canister. The additional subcutaneous electrode 13' is essentially identical to the previously described electrode. In this embodiment the cardioversion/defibrillation energy is delivered between the active surface of the canister and the two coil electrodes 27 and 27'. Additionally, provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
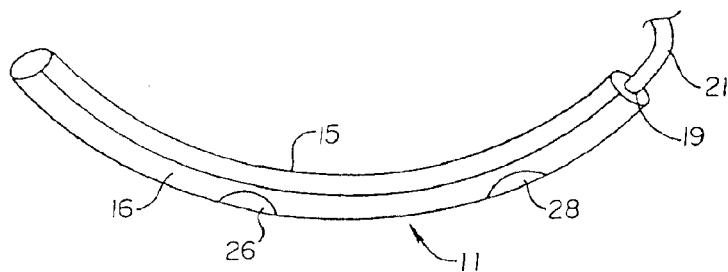
FIG. 12 is a schematic view of yet a further embodiment where the canister of the S-ICD of the present invention is shaped to be particularly useful in placing subcutaneously adjacent and parallel to a rib of a patient.
Figure 13:
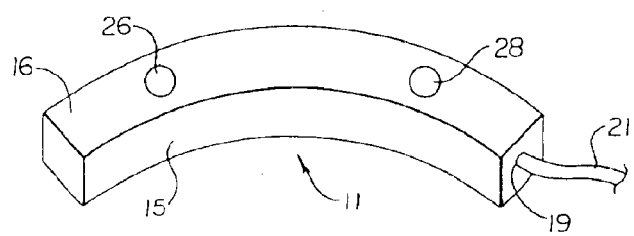
FIG. 13 is a schematic of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm without 1 cm being presently preferred. Alternatively, instead of having a circular cross sectional area, the canister could have a rectangular or square cross sectional area as illustrated in FIG. 13 without falling outside of the scope of the present invention. The length of the canister can vary depending on the size of the patient's thorax. Currently the canister is about 5 cm to about 15 cm long with about being presently preferred. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 35 cm depending on the size of the patient. Additionally, the radius of the curvature need not be uniform throughout the canister such that it can be shaped closer to the shape of the ribs. The canister has an active surface, 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface of the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

FIGS. 14 to 18 depict particular US-ICD embodiments of the present invention. The various sensing, shocking and pacing circuitry, described in detail above with respect to the S-ICD embodiments, may additionally be incorporated into the following US-ICD embodiments. Furthermore, particular aspects of any individual S-ICD embodiment discussed above, may be incorporated, in whole or in part, into the US-ICD embodiments depicted in the following figures.

Figure 14:
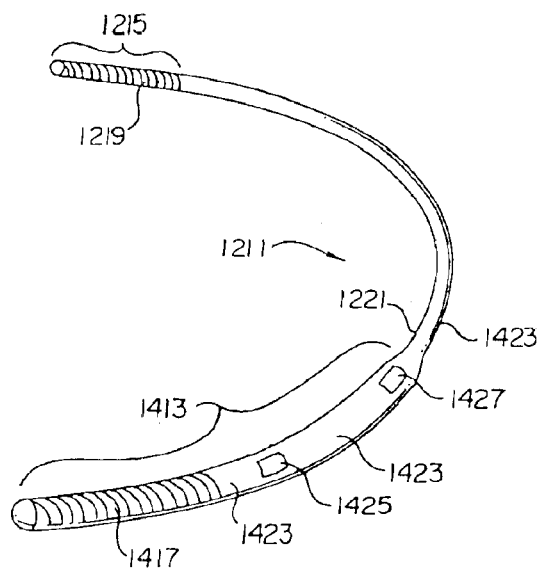
FIG. 14 is a schematic view of a Unitary Subcutaneous ICD (US-ICD) of the present invention.

Turning now to FIG. 14, the US-ICD of the present invention is illustrated. The US-ICD consists of a curved housing 1211 with a first and second end. The first end 1413 is thicker than the second end 1215. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillation electrodes 1417 and 1219 located on the outer surface of the two ends of the housing. The circuitry can provide cardioversion/defibrillation energy in different types of waveforms. In the preferred embodiment, a 100 uF biphasic waveform is used of approximately 10–20 ms total duration and with the initial phase containing approximately $2/3$ of the energy, however, any type of waveform can be utilized such as monophasic, biphasic, multiphasic or alternative waveforms as is known in the art.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy, intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller.

The two cardioversion/defibrillation electrodes on the housing are used for delivering the high voltage cardioversion/defibrillation energy across the heart. In the preferred embodiment, the cardioversion/defibrillation electrodes are coil electrodes, however, other cardioversion/defibrillation electrodes could be used such as having electrically isolated active surfaces or platinum alloy electrodes. The coil cardioversion/defibrillation electrodes are about 5–10 cm in length. Located on the housing between the two cardioversion/defibrillation electrodes are two sense electrodes 1425 and 1427. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 1423. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

Figure 15:
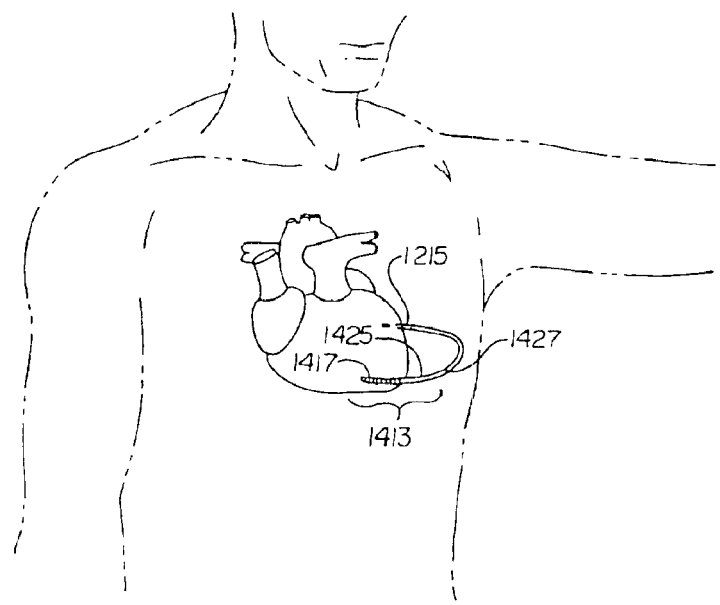
FIG. 15 is a schematic view of the US-ICD subcutaneously implanted in the thorax of a patient.

Turning now to FIG. 15, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 16:
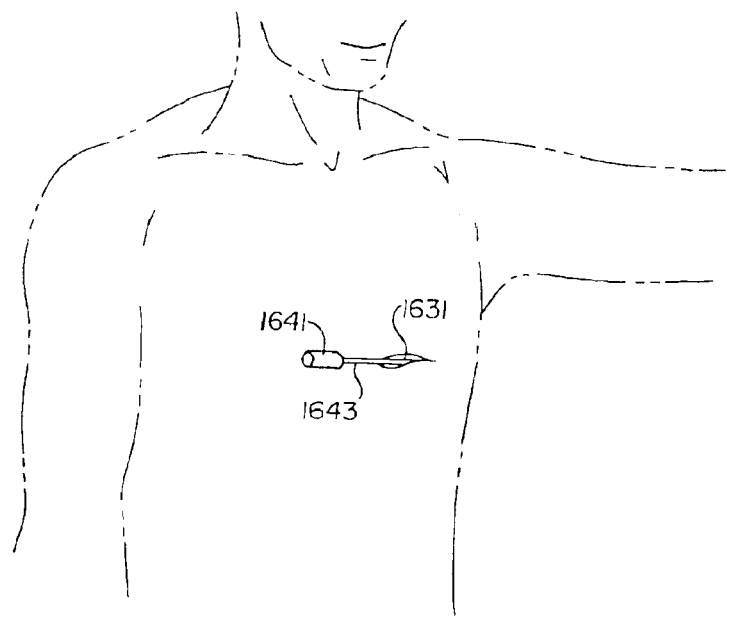
FIG. 16 is a schematic view of the method of making a subcutaneous path from the preferred incision for implanting the US-ICD.
Figure 17:
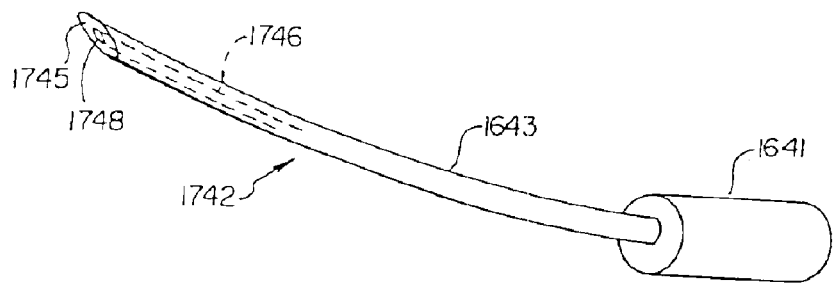
FIG. 17 is a schematic view of an introducer for performing the method of US-ICD implantation.

FIG. 16 schematically illustrates the method for implanting the US-ICD of the present invention. An incision 1631 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 1742 (see FIG. 17). The trocar has a proximal handle 1641 and a curved shaft 1643. The distal end 1745 of the trocar is tapered to allow for dissection of a subcutaneous path in the patient. Preferably, the trocar is cannulated having a central lumen 1746 and terminating in an opening 1748 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 18:
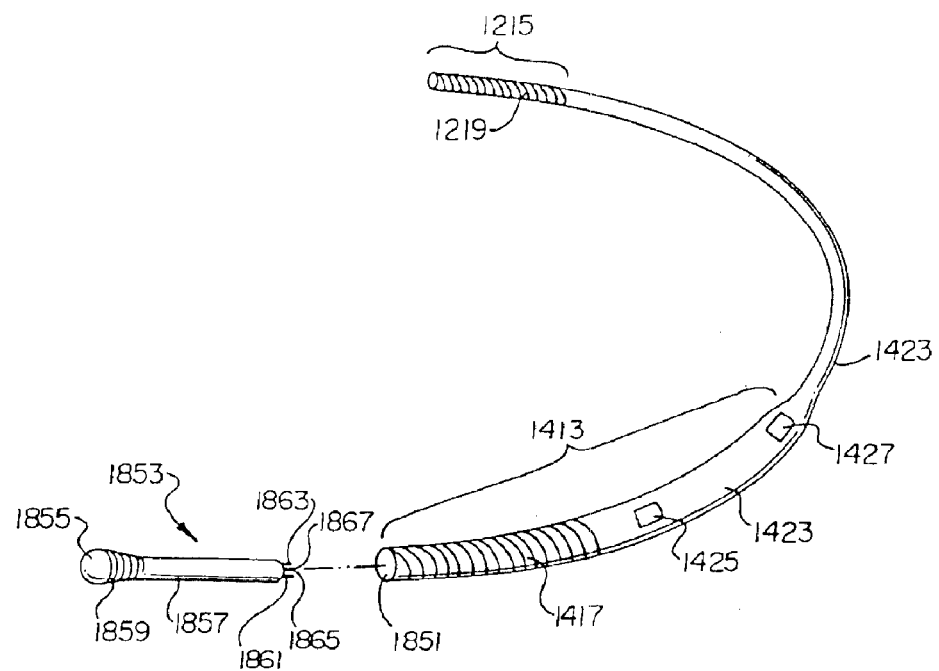
FIG. 18 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 18, a different embodiment is schematically illustrated in exploded view which provides different sized US-ICDs that are easier to manufacture. The different sized US-ICDs will all have the same sized and shaped thick end 1413. The thick end is hollow inside allowing for the insertion of a core operational member 1853. The core member comprises a housing 1857 which contains the battery supply, capacitor and operational circuitry for the US-ICD. The proximal end of the core member has a plurality of electronic plug connectors. Plug connectors 1861 and 1863 are electronically connected to the sense electrodes via pressure fit connectors (not illustrated) inside the thick end which are standard in the art. Plug connectors 1865 and 1867 are also electronically connected to the cardioverter/defibrillator electrodes via pressure fit connectors inside the thick end. The distal end of the core member comprises an end cap 1855, and a ribbed fitting 1859 which creates a water-tight seal when the core member is inserted into opening 1851 of the thick end of the US-ICD.

The core member of the different sized and shaped US-ICD will all be the same size and shape. That way, during an implantation procedure, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

To ensure adequate pacing capture of the heart through an S-ICD having a subcutaneous only lead system, pacing therapy needs to be considerably enhanced by using a biphasic rather than the conventional monophasic waveform for pacing. In addition, to further compensate for the lack of direct contact with the heart, the subcutaneous electrode system, especially the anterior thoracic electrode system, that will be delivering the ATP stimuli should result in as lugh as a current density as possible in order to activate the cardiac tissues. This can be facilitated by using a small electrode as close to the sternum as possible In the tissues overlying the right ventricle, the cardiac chamber closest to rho anterior subcutaneous space where the S-ICD of the present invention will lie.

Figure 19:
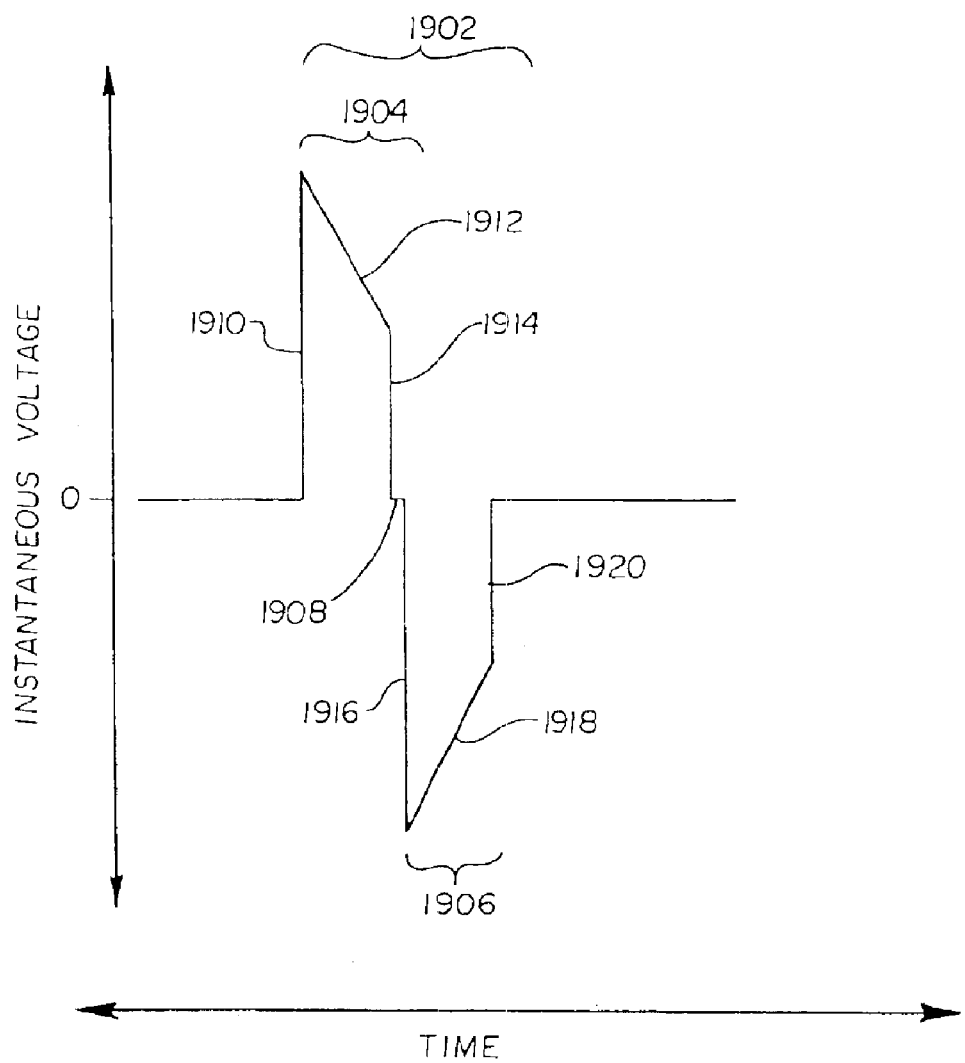
FIG. 19 is a graph that shows an example of a biphasic waveform for use in anti-tachycardia pacing in an embodiment of the present invention.

FIG. 19 is a graph that shows an embodiment of the example of a biphasic waveform for use in ATP applications in S-ICD and US-ICD devices in an embodiment of the present invention. As shown in FIG. 19, the biphasic waveform is plotted as a function of time versus instantaneous voltage.

In an embodiment, the biphasic waveform 1902 comprises a positive portion 1904, a negative portion 1906 and a transition portion 1908. The positive portion 1904 of the biphasic waveform 1902 comprises an initial positive voltage 1910, a positive decay voltage 1912 and a final positive voltage 1914. The negative portion 1906 of the biphasic waveform 1902 comprises an initial negative voltage 1916, a negative decay voltage 1918 and a final negative voltage 1920. In an embodiment, the polarities of the biphasic waveform 1902 can be reversed such that the negative portion 1906 precedes the positive portion 1904 in time.

As shown in FIG. 19, the biphasic waveform 1902 is initially at zero voltage. Upon commencement of ATP, a voltage of positive polarity is provided and the biphasic waveform 1902 rises to the initial positive voltage 1910. Next, the voltage of the biphasic waveform 1902 decays along the positive decay voltage 1912 until reaching a voltage level at the final positive voltage 1914. At this point, the positive portion 1904 of the biphasic waveform 1902 is truncated and a negative voltage is provided. The biphasic waveform 1902 then undergoes a relatively short transition portion 1908 where the voltage is approximately zero. Next, the biphasic waveform 1902 is increased (in absolute value) in the opposite (negative) polarity to the initial negative voltage 1916. After reaching its maximum negative voltage (in absolute value), the voltage of the biphasic waveform 1902 decays along the negative decay voltage 1918 until reaching a voltage level at the final negative voltage 1914. After the negative portion 1906 of the biphasic waveform 1902 is truncated at the final negative voltage 1914, the biphasic waveform 1902 returns to zero.

The total amount of time that the biphasic waveform 1902 comprises is known as the "pulse width." In an embodiment, the pulse width of the biphasic waveform can range from approximately 2 milliseconds to approximately 40 milliseconds. The total amount of energy delivered is a function of the pulse width and the average (absolute) value of the voltage. The ratio of the final positive voltage 1914 (or final negative voltage 1920) to the initial positive voltage 1910 (initial negative voltage 1916) is known as the "tilt" of the waveform. Typically, the tilt of the positive portion 1904 of the biphasic waveform 1902 is equal to the negative portion 1906. However, depending upon the specific application, these two tilts may be different from each other.

An example of one embodiment of the biphasic waveform 1902 will now be described. In this embodiment, the amplitude of the initial positive voltage 1910 can range from approximately 5 to approximately 500 volts. In one example, the amplitude of the initial positive voltage 1910 is approximately 20 volts. In addition, in an example, the tilt of the positive decay voltage 1912 is approximately 50%. Typically, the tilt of the positive decay voltage 1912 can range from approximately 10% to approximately 90% although the waveform tilt can be considerably higher or lower, depending on variables such as capacitance, tissue resistance and type of electrode system used. Assuming a 50% tilt for this example, the amplitude of the trailing edge of the final positive voltage 1914 is approximately 10 volts, but can vary between approximately 2 volts to approximately 300 volts.

Similarly, the amplitude of the initial negative voltage 1916 can range from approximately -5 to approximately -500 volts. In one example, the amplitude of the initial negative voltage 1916 is approximately -20 volts. In addition, in an example the tilt of the negative decay voltage 1918 is approximately 50%. Typically, the tilt of the negative decay voltage 1918 can range from approximately 10% to approximately 90%. However, like the initial positive phase described above, the tilt and amplitude of an effective pacing pulse may vary considerably. Assuming a 50% tilt for this example, the amplitude of the final negative voltage is approximately -10 volts, but can vary between approximately -2 volts to approximately -300 volts. However, if the pacing stimulus has a very short duration, the tilt may be high.

In the example, the pulse width of the biphasic waveform 1902 can range from approximately 2 milliseconds to approximately 40 milliseconds. In addition, the implantable cardioverter-defibrillator employs anti-tachycardia pacing at rates of approximately 100 to approximately 300 stimuli/minute for ventricular tachycardia episodes. In addition, up to 30 ATP stimuli for any single attempt could be allowed and as many as 15 ATP attempts could be allowed for any effort to terminate a single episode of VT. One might also allow for different ATP methods to be employed for VTs of different rates or ECG characteristics. Moreover, the device may be allowed to auto-select the method of ATP to be used based upon the device's and/or the physician's experience with previous episodes of VT or with the patient's underlying cardiac condition.

Although it possible for the present invention to provide standard ATP at predetermined or preprogrammed rates for monomorphic VT, the use of an S-ICD may also be employed for the treatment of other arrhythmias such as atrial tachyarrhythmias. In another embodiment, the invention can provide ATP in response to a certain activity, respiration, pressure or oxygenation sensor as coupled to arrhythmia characteristics.

The S-ICD and US-ICD devices and methods of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. A method of treating an abnormal cardiac rhythm comprising:

providing an implantable stimulus device in a patient, the implantable stimulus device including a power source and an energy storage system;

providing a lead system for the stimulus device, the step of providing the lead system including a process resulting in implantation of the leads only to areas that are exclusive of the patient's heart;

sensing an event in the patient's cardiac rhythm;

coupling the power source to the energy storage system to transfer energy to the energy storage system;

storing energy in the energy storage system; and discharging the energy from the energy storage system using the lead system to a subcutaneous volume of the patient;

wherein the lead system includes a first electrode and the implantable stimulus device includes a second electrode on a housing thereof, wherein the steps of providing the stimulus device and providing the lead assembly are performed such that a straight line drawn from the first electrode to the second electrode would intersect a portion of the heart, and the step of discharging energy from the energy storage system includes discharging energy between the first electrode and the second electrode.

2. The method of claim 1, wherein the step of sensing an event in the patient's cardiac rhythm is performed in order to detect an abnormally fast heart rhythm.

3. The method of claim 2, wherein:
the steps of storing energy and discharging the energy are repeated at an initial rate set to overdrive the abnormally fast heart rhythm until the heart is captured for pacing purposes; and, then,
a rate at which the steps of storing energy and discharging energy are performed is reduced.

4. The method of claim 3, wherein the initial rate is in the range of 100 to 300 stimuli per minute.

5. The method of claim 1, wherein the step of providing an implantable stimulus device includes implanting the stimulus device subcutaneously between approximately the third rib and the twelfth rib of the patient.

6. The method of claim 1, wherein the step of providing an implantable stimulus device includes implanting the stimulus device at about the left axillary line with the lead system including a lead extending medially therefrom.

7. The method of claim 1, wherein the step of providing an implantable stimulus device includes placing the stimulus device at a subcutaneous location along the inframammary crease of the patient.

8. The method of claim 1, wherein the step of discharging the energy is performed to produce a biphasic waveform.

9. A method of treating an abnormal cardiac rhythm comprising:
providing an implantable stimulus device in a patient, the implantable stimulus device including a power source and an energy storage system;
providing a lead system for the stimulus device, the step of providing the lead system including a process resulting in implantation of the leads only to areas that are exclusive of the patient's heart;
sensing an event in the patient's cardiac rhythm;
coupling the power source to the energy storage system to transfer energy to the energy storage system;
storing energy in the energy storage system; and
discharging the energy from the energy storage system using the lead system to a subcutaneous volume of the patient;
wherein the step of providing an implantable stimulus device includes implanting the stimulus device at about the left axillary line with the lead system including a lead extending medially therefrom.

10. A method of treating an abnormal cardiac rhythm comprising:
providing an implantable stimulus device in a patient, the implantable stimulus device including a power source and an energy storage system;
providing a lead system for the stimulus device, the step of providing the lead system including a process resulting in implantation of the leads only to areas that are exclusive of the patient's heart;
sensing an event in the patient's cardiac rhythm;
coupling the power source to the energy storage system to transfer energy to the energy storage system;
storing energy in the energy storage system; and
discharging the energy from the energy storage system using the lead system to a subcutaneous volume of the patient;
wherein the step of providing an implantable stimulus device includes placing the stimulus device at a subcutaneous location along the inframammary crease of the patient.

11. A method of treating tachycardia comprising:
providing an implantable stimulus device subcutaneously in a patient to a location at approximately the left anterior axillary line of the patient between the third and the twelfth ribs, the implantable stimulus device including a power source and an energy storage system;
providing a lead system for the stimulus device by passing the lead system to locations exclusive of the patient's heart;
sensing events in the patient's cardiac rhythm to determine whether an abnormally fast heart rhythm is occurring; and if so, repeating the following steps at an initial rate to overdrive the abnormally fast heart rhythm:
coupling the power source to the energy storage system to transfer energy to the energy storage system;
storing energy in the energy storage system; and
discharging the energy from the energy storage system via first and second electrodes disposed within the patient exclusive of the patient's heart, in a biphasic waveform;
and then repeating the steps at a reduced rate.

12. The method of claim 11, wherein both the first and second electrodes are part of the lead system.

13. The method of claim 11, wherein the first electrode is part of the lead system and the second electrode is disposed on a housing for the implantable cardioverter-defibrillator.

14. A method of treating an abnormal cardiac rhythm comprising:
providing an implantable stimulus device in a patient, the implantable stimulus device including a power source and an energy storage system;
providing a lead system for the stimulus device, the step of providing the lead system including a process resulting in implantation of the leads only to areas that are exclusive of the patient's heart;
sensing an event in the patient's cardiac rhythm;
coupling the power source to the energy storage system to transfer energy to the energy storage system;
storing energy in the energy storage system; and
discharging the energy from the energy storage system using the lead system to a subcutaneous volume of the patient; wherein:
the step of sensing an event in the patient's cardiac rhythm is performed in order to detect an abnormally fast heart rhythm; and
the steps of storing energy arid discharging the energy are repeated at an Initial rate set to overdrive the abnormally fast heart rhythm until the heart is captured for pacing purposes and, then, a rate at which the steps of storing energy and discharging energy are performed is reduced.

15. The method of claim 14, wherein the lead system includes a first electrode and the implantable stimulus device includes a second electrode on a housing thereof, wherein the steps of providing the stimulus device and providing the lead assembly are performed such that a straight line drawn from the first electrode to the second electrode would intersect a portion of the heart, and the step of discharging energy from the energy storage system includes discharging energy between the first electrode and the second electrode.

* * * * *

UNITED STATES PATENT AND TRADEMARK OFFICE
CERTIFICATE OF CORRECTION

PATENT NO. : 6,856,835 B2  Page 1 of 1
DATED : February 15, 2005
INVENTOR(S) : Gust H. Bardy et al.

It is certified that error appears in the above-identified patent and that said Letters Patent is hereby corrected as shown below:

Column 7,
Line 44, delete "14", and insert therefor -- 10 --.

Column 8,
Line 2, delete "arid", insert therefor -- and --.

Column 10,
Line 2, delete "(sec", insert therefor -- (see --.
Line 5, delete "apace", insert therefor -- space --.

Column 12,
Line 26, delete "cardioversion/defibrillation electrodes", and insert therefor
-- cardioversion/defibrillating electrodes --.

Column 14,
Line 52, delete "lugh", insert therefor -- high --.
Line 56, delete "rho", insert therefor -- the --.

Column 18,
Line 46, delete "arid", insert therefor -- and --.

Signed and Sealed this

Seventeenth Day of May, 2005

JON W. DUDAS
*Director of the United States Patent and Trademark Office*